United States Patent
Neubauer et al.

(10) Patent No.: US 9,271,802 B2
(45) Date of Patent: Mar. 1, 2016

(54) MALLEOLAR REGISTRATION CLAMP AND MALLEOLAR REGISTRATION METHOD

(75) Inventors: Timo Neubauer, Grasbrunn-Neukeferloh (DE); Manuel Millahn, München (DE); Norman Plaβky, Erfurt (DE)

(73) Assignee: Brainlab AG, Feldkirchen (DE)

( * ) Notice: Subject to any disclaimer, the term of this patent is extended or adjusted under 35 U.S.C. 154(b) by 646 days.

(21) Appl. No.: 13/387,138

(22) PCT Filed: Jul. 31, 2009

(86) PCT No.: PCT/EP2009/059946
§ 371 (c)(1),
(2), (4) Date: Jan. 26, 2012

(87) PCT Pub. No.: WO2011/012169
PCT Pub. Date: Feb. 3, 2011

(65) Prior Publication Data
US 2012/0123299 A1    May 17, 2012

(51) Int. Cl.
*A61B 5/103* (2006.01)
*A61B 19/00* (2006.01)
(52) U.S. Cl.
CPC ..... *A61B 19/5244* (2013.01); *A61B 2019/5416* (2013.01); *A61B 2019/5483* (2013.01)
(58) Field of Classification Search
CPC ..... A61B 5/4528; A61B 5/103; A61B 5/0053
USPC ......................................... 600/587
See application file for complete search history.

(56) References Cited

U.S. PATENT DOCUMENTS

| | | | |
|---|---|---|---|
| 5,335,674 A * | 8/1994 | Siegler | 600/595 |
| 5,435,009 A | 7/1995 | Schild et al. | |
| 5,611,353 A * | 3/1997 | Dance et al. | 600/595 |
| 5,893,553 A * | 4/1999 | Pinkous | 269/249 |
| 6,708,966 B1 * | 3/2004 | Troudt | 269/249 |
| 2002/0193717 A1 | 12/2002 | Burns et al. | |
| 2003/0153829 A1 * | 8/2003 | Sarin et al. | 600/426 |
| 2004/0097952 A1 * | 5/2004 | Sarin et al. | 606/102 |
| 2004/0102792 A1 | 5/2004 | Sarin et al. | |
| 2004/0172044 A1 * | 9/2004 | Grimm et al. | 606/130 |
| 2004/0254586 A1 * | 12/2004 | Sarin et al. | 606/130 |
| 2005/0096535 A1 * | 5/2005 | de la Barrera | 600/424 |

(Continued)

FOREIGN PATENT DOCUMENTS

| | | |
|---|---|---|
| DE | 100 31 887 A1 | 1/2002 |
| DE | 100 45 376 A1 | 4/2002 |

(Continued)

OTHER PUBLICATIONS

International Search Report for International Patent Application No. PCT/EP2009/059946 dated Jun. 1, 2010 (resubmitted with correct date).

*Primary Examiner* — Sean Dougherty
*Assistant Examiner* — Daniel Cerioni
(74) *Attorney, Agent, or Firm* — Tucker Ellis LLP; Michael E. Hudzinski (57) ABSTRACT

A malleolar registration clamp comprising a reference unit and a receiving portion for receiving the malleolus, wherein the receiving portion is designed to receive at least part of the malleolus in a defined position relative to the receiving portion, and the position of the reference unit relative to the receiving portion is defined.

5 Claims, 5 Drawing Sheets

(56) References Cited

U.S. PATENT DOCUMENTS

| | | | |
|---|---|---|---|
| 2005/0113677 A1* | 5/2005 | Davies et al. | 600/424 |
| 2005/0245820 A1* | 11/2005 | Sarin | 600/429 |
| 2006/0084889 A1 | 4/2006 | Drumm et al. | |
| 2008/0033442 A1* | 2/2008 | Amiot et al. | 606/80ke |
| 2008/0045972 A1 | 2/2008 | Wagner et al. | |
| 2010/0063508 A1* | 3/2010 | Borja et al. | 606/88 |

FOREIGN PATENT DOCUMENTS

| | | |
|---|---|---|
| EP | 1 569 554 | 2/2007 |
| WO | 96/29940 | 10/1996 |
| WO | 2008/036167 A2 | 3/2008 |

* cited by examiner

MALLEOLAR REGISTRATION CLAMP AND MALLEOLAR REGISTRATION METHOD

This application is a national phase of International Application No. PCT/EP2009/059946 filed Jul. 31, 2009 and published in the English language.

FIELD OF THE INVENTION

The present invention relates to a clamp and a method for registering one or more malleoli.

BACKGROUND OF THE INVENTION

For surgery, especially knee surgery, it is often necessary to know the position of one or both malleoli of an ankle. Determining the position is also called registration if it implies informing a navigation system of said position in a reference system of the navigation system. A malleolar registration clamp and a malleolar registration method are used for registering one or more malleoli.

A navigation system and/or surgical navigation system is understood to mean a system consisting of: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) comprises in particular a processor (CPU), a working memory, advantageously an indicating facility (for example, a visual indicating facility such as a monitor and/or an audio indicating facility such as a loudspeaker) and advantageously a permanent data memory, wherein the data processing device processes navigation data forwarded to it by the receiver and can advantageously output guidance information to a user via the indicating facility. The navigation data can be stored in the permanent data memory and for example compared with data which have been stored in said memory beforehand.

SUMMARY OF THE INVENTION

Document WO 2008/036167 A2 discloses a boot for immobilising the foot, wherein there is negligible movement of the boot relative to the leg. A tracking device is attached to the boot. The boot has openings, such that the medial and lateral malleolus can be accessed for registering, for example using a pointer.

The object to be solved by the present invention is to provide a clamp and a method which allow easy and automatic malleolar registration. This object is solved by a clamp, a method, a computer program, a computer and a system according to the independent claims herein. Further embodiments are specified in the dependent claims.

A malleolar registration clamp in accordance with the present invention comprises a reference unit and a receiving portion for receiving the malleolus. The receiving portion is designed to receive the malleolus in a defined position relative to the receiving portion, and the position of the reference unit relative to the receiving portion is defined. This "defined" relative position is understood to mean that the position of two components relative to each other is invariant and known. In this document, the term "position" is understood to mean a spatial location or a combination of a spatial location and a rotational alignment, wherein the location and the alignment can comprise up to three dimensions each.

A reference unit, also referred to as a marker device, can be a reference star or one or more markers. The function of a marker is to be detected by a marker detection device (for example, a camera or an ultrasound receiver), such that its position (i.e. its spatial location and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and may therefore be referred to as a marker sphere; markers can also, however, exhibit a cornered—for example, cube-shaped—shape.

A "reference star" refers to a device which a number of markers, advantageously three markers, are attached to, wherein the markers are attached to the reference star such that they are stationary and advantageously such that they can be detached, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is thus also then possible for the objects (for example, instruments and/or parts of a body) to which the reference star is attached to be identified and/or differentiated from each other. In a surgical navigation method, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to. Where it is clear from the context, the term "reference star" can also refer to a reference star comprising at least one marker attached to it. Such a system consisting of a reference star and at least one marker can also be referred to as a marker star.

The receiving portion has a shape which is such that the malleolus assumes a defined position within the receiving portion, such that the relative position—or at least the relative spatial location—between the malleolus and the receiving portion is unambiguous. The receiving portion has an opening or recess for receiving the malleolus or at least a part of the malleolus. Preferably, the malleolus is in point contact or area contact with the receiving portion.

In one embodiment, the receiving portion has a concave shape, for example the shape of a cup, in particular a hemispherical cap. Preferably, the shape of the receiving portion is the inverse of the shape of the malleolus. The shape of the receiving portion is preferably such that the receiving portion centres itself on the malleolus when it is pressed against the malleolus.

The clamp preferably comprises a body, i.e. the clamp body, which is of any suitable shape. One possible shape is a C-shaped arc with the two ends of the arc facing each other.

The receiving portion is then preferably located at one end of the arc. The clamp body can also have a boot-like shape or the shape of shin guard. The receiving portion is then either a part of the clamp body or a separate component having a defined and known position relative to the clamp body.

Preferably, the clamp body has two parts which exhibit a variable relative position, wherein the receiving portion and the reference unit are arranged on the first clamp body part and can therefore be referred to as the first receiving portion and the first reference unit, respectively. Using such a two-part clamp body, the clamp can be easily applied and adjusted to patients of different sizes. Since the receiving portion and the reference unit are arranged on the first clamp body part, their relative position and therefore the relative position between the reference unit and the malleolus is known.

The malleolus registration clamp also preferably comprises a second receiving portion arranged on the second clamp body part, for receiving a second malleolus in a defined position relative to the second receiving portion. Using such a configuration, the clamp functions as a gripper, with the two receiving portions pressing on the two malleoli. This results in a tight fit of the clamp on the ankle.

Preferably, the second receiving portion of the second clamp body part faces the first receiving portion of the first clamp body part, such that a patient's ankle can be securely gripped between the two receiving portions.

In one embodiment of the invention, the malleolar registration clamp comprises a second reference unit on the second clamp body part, wherein the position of the second reference unit relative to the second receiving portion is defined. The second reference unit is used to register the second malleolus. If the first reference unit is a 3D reference unit and the relative position between the two clamp body parts is only variable in one rotational or translational dimension, it is sufficient for the second reference unit to be a one-dimensional reference unit, for example a single marker sphere, since the second reference unit can only move along a known trajectory which is either a straight line or a circular arc. A 3D reference unit allows the position of the reference unit to be determined in up to three translational dimensions and/or in up to three rotational dimensions. A one-dimensional reference unit, for example a single marker sphere, generally allows the spatial location of the reference unit to be determined in one dimension only. However, if the spatial location of the one-dimensional reference unit is constrained, it is possible to determine the position in up to three spatial dimensions and three rotational dimensions.

In one embodiment, the second clamp body part is a screw within a thread of the first clamp body part. In this configuration, screwing the second clamp body part generates a linear, one-dimensional translational movement of the second receiving portion. By turning the screw, the ankle can be gripped between the two receiving portions.

In accordance with a second embodiment, the first clamp body part and the second clamp body part are connected by a link, for example a hinge joint or a rail link. Preferably, the relative position between the first and second receiving portions can be adjusted via the link. The distance between the first and second receiving portions can preferably be adjusted within a range of 3 cm to 12 cm, in particular 5 cm to 8 cm.

The link preferably exhibits one degree of freedom between the first and second clamp body parts. The hinge joint, for example, has exactly one rotational degree of freedom but no translational degree of freedom. In one embodiment, the link—i.e. for example the hinge joint—is spring-loaded, such that the spring presses the two receiving portions of the two clamp body parts against each other. In this embodiment, the receiving portions press against the two malleoli, thereby centering themselves on the malleoli, without further manipulation of the clamp. In a second embodiment, an adjustment screw is provided for adjusting the relative rotational or translational alignment between the first clamp body part and the second clamp body part. This embodiment has the advantage that, once the adjusting screw has been set, unintentional loosening of the clamp is impossible.

The present invention also relates to a malleolar registration method comprising the steps of: providing reference unit position data representing the position of the reference unit of a malleolar registration clamp as explained above; providing contact data indicating whether or not the malleolus has been received within the receiving portion of the registration clamp in a defined position relative to the receiving portion; providing receiving portion position data representing the position of the receiving portion relative to the reference unit; providing malleolar position data representing the position of the malleolus relative to the receiving portion; and registering the malleolus by calculating the position of the malleolus from the reference unit position data, the receiving portion position data and the malleolar position data, if the contact data indicate that the malleolus has been received in a defined position relative to the receiving portion.

Where data are "provided", this means that they are ready for use by the method in accordance with the invention. The data can achieve this state of being "provided" for example by being detected or captured (for example by analysis apparatus) or by being inputted (for example via interfaces). The contact data, for example, can be provided by pressing a key or button when the malleolus is received within the receiving portion in a defined position relative to the receiving portion, i.e. when the clamp is applied correctly. The data can also have this state by being stored in a memory (for example a ROM, CD, hard drive) and thus ready for use within the framework of the method in accordance with the invention.

A malleolar registration clamp as described above is for example applied to a patient, and the position of the reference unit is detected, for example using a navigation system, thus generating reference unit position data. In accordance with the present invention, the clamp is applied such that the malleolus is in a defined position relative to the receiving portion, and the malleolus is registered by calculating the malleolar position from the position of the reference unit, the relative position between the reference unit and the receiving portion and the relative position between the receiving portion and the malleolus.

In one embodiment of the invention, the malleolar registration method also includes the steps of: providing second contact data indicating whether or not a second malleolus has been received within a second receiving portion of the registration clamp in a defined position relative to the second receiving portion; providing second malleolar position data representing the position of the second malleolus relative to the second receiving portion; providing second reference unit position data representing the position of the second reference unit; and registering the second malleolus by calculating the malleolar position from the second reference unit position data, the second receiving portion position data and the second malleolar position data, if the second contact data indicate that the second malleolus has been received in a defined position relative to the second receiving portion.

A two-part clamp, i.e. a clamp comprising a clamp body consisting of two clamp body parts, is for example used and applied such that a second malleolus is received in a defined position relative to the second clamp body part. In this embodiment, the first malleolus is still in a defined position relative to the first clamp body part. This embodiment ensures a proper rotational alignment of the first malleolus in the receiving portion of the first clamp body part in at least two rotational dimensions. This means that the axis between the two malleoli can also be reliably calculated.

The second malleolus is registered by calculating the malleolar position from the position of the second reference unit, the relative position between the second reference unit and the second receiving portion and the relative position between the second receiving portion and the second malleolus. This means that both the malleoli are registered, using the first reference unit and the second reference unit, respectively. If both the reference units are 3D reference units, the two malleoli can be registered independently.

The second reference unit position data can optionally be derived from the reference unit position data and the position of the second reference unit relative to the reference unit. If only one of the reference units is a 3D reference unit, and the other reference unit is a one-dimensional reference unit, then the malleolus in the receiving portion of the clamp body part comprising the 3D reference unit is registered first, as explained above, and then the malleolus in the receiving unit of the other clamp body part is registered, based on the position of the 3D reference unit and the position of the one-dimensional reference unit relative to the 3D reference unit. This is possible if the relative movement of the two clamp body parts, and therefore the two reference units, is constrained for example to a one-dimensional relative movement.

The method in accordance with the invention is in particular a data processing method. The data processing method is preferably performed using technical means, in particular a computer. The computer in particular comprises a processor and a memory in order to process the data, in particular electronically. The calculating steps described are in particular performed by a computer.

The present invention also relates to a computer program which, when it is running on a data processing apparatus or is loaded onto a data processing apparatus, causes the data processing apparatus to perform the method as explained above, and/or to a storage medium on which such a program is stored, and/or to a data processing apparatus on which the program is run or in the memory of which the program is loaded, and/or to a signal wave, in particular a digital signal wave, comprising information describing the program and/or comprising the method steps of the method as explained above.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Such a system can be a computer; a computer can be a data processing device comprising means for executing the computer program elements and/or the program in accordance with the invention. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s). The computer and/or data processing device can in particular constitute a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated in an instrument).

The invention also relates to a computer on which the program as explained above is loaded or stored or executed.

The invention also relates to a malleolar registration system comprising a clamp and a computer as explained above and a registration unit for registering the position of the reference unit or units. The registration unit or units can be part of a medical navigation system. The registration unit is a detection device for the position of the reference unit.

The computer of the malleolar registration system can comprise a processor for registering the malleolus by calculating the malleolar position from the position of the reference unit, the relative position between the reference unit and the receiving portion and the relative position between the receiving portion and the malleolus. The position of the reference unit is registered using a 3D camera, resulting for example in a known position of the reference unit relative to the 3D camera or any other reference. Starting from this position, and incorporating the relative position between the reference unit and the receiving portion and the relative position between the receiving portion and the malleolus, it is then possible to calculate the position of the malleolus relative to the 3D camera or any other reference.

BRIEF DESCRIPTION OF THE DRAWINGS

The present application shall now be explained in more detail by referring to two example embodiments illustrated in the accompanying figures which show.

DETAILED DESCRIPTION

Figure 1:
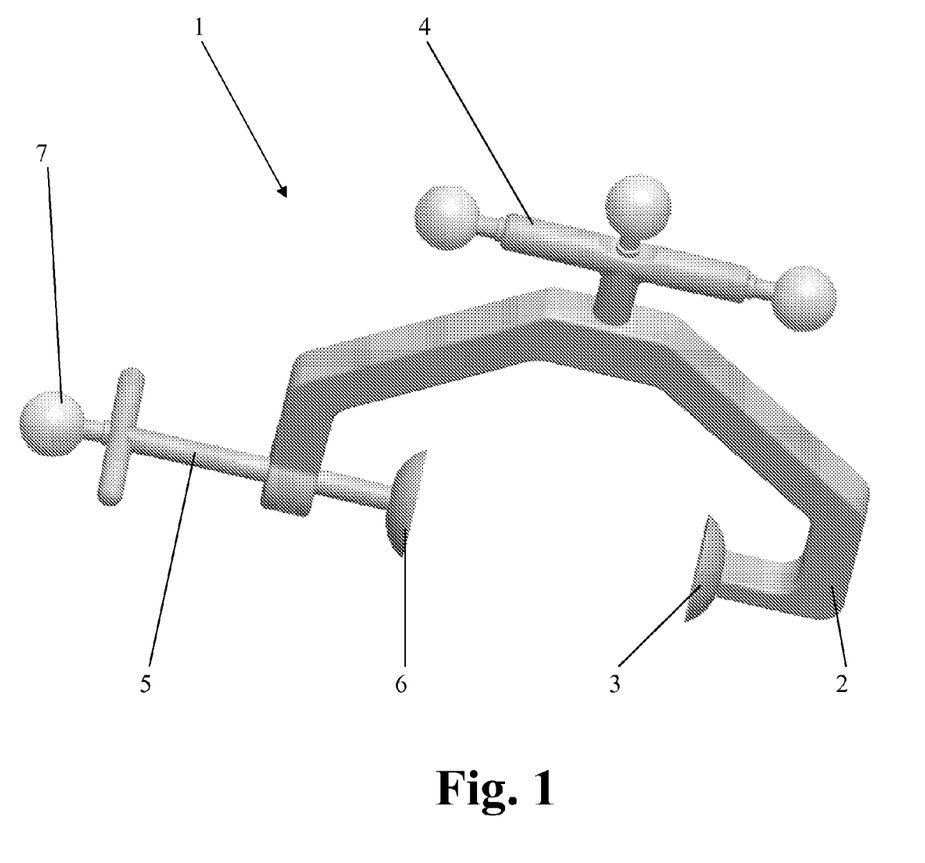
FIG. 1 a first embodiment of a malleolar registration clamp.

FIG. 1 shows a malleolar registration clamp 1 comprising a body consisting of a first clamp body part 2 and a second clamp body part 5. A (first) reference unit 4 and a (first) receiving portion 3 are attached to the first clamp body part 2. The first clamp body part 2 is C-shaped. The reference unit 4 is a reference star comprising three marker spheres in a three-dimensional arrangement. Using a marker detection device, it is possible to detect the position of the reference unit 4 and therefore the position of an object connected to the reference unit 4. The term "position" is understood here to mean the spatial location in up to three translational dimensions, the orientation or alignment in up to three rotational dimensions, or a combination of these.

The second clamp body part 5 is a screw which is located within a thread of the first clamp body part 2. The second clamp body part 5 comprises a second receiving portion 6 at one of its axial ends and is orientated such that the opening of the second receiving portion 6 faces the opening of the receiving portion 3 of the first clamp body part 3.

A second reference unit 7 consisting of a single marker sphere is also attached to the second clamp body part 5. The reference unit 7 is located at the opposite axial end of the second clamp body part 5 to the axial end at which the second receiving portion 6 is located. When the screw-like second clamp body part 5 is turned, this rotation generates a translational movement of the second clamp body part 5 along its longitudinal axis, thus changing the distance between the second receiving portion 6 and the receiving portion 3. At the same time, the second reference unit 7 follows a known linear trajectory, i.e. the second reference unit 7 can only exhibit a limited and defined position relative to the first reference unit 4. Due to this constraint, a single marker sphere is sufficient as the second reference unit, in order to unambiguously detect the position of the second reference unit 7 relative to the first reference unit 4 and therefore the position of the second clamp body part 5 relative to the first clamp body part 2 and also the position of the second receiving portion 6 relative to the receiving portion 3.

In a modification of this embodiment (not shown in the figures), the second reference unit 7 is located on the side of the second clamp body part 5 at a distance from its rotational axis which is larger than zero, i.e. when the second clamp body part 5 is adjusted, the second reference unit 7 follows a trajectory which has the shape of a helix. Since the diameter of this helix and its position relative to the reference unit 4 are known, the position of the second reference unit 7 relative to the reference unit 4 can then be determined, even if it only consists of a single marker sphere.

Figure 2:
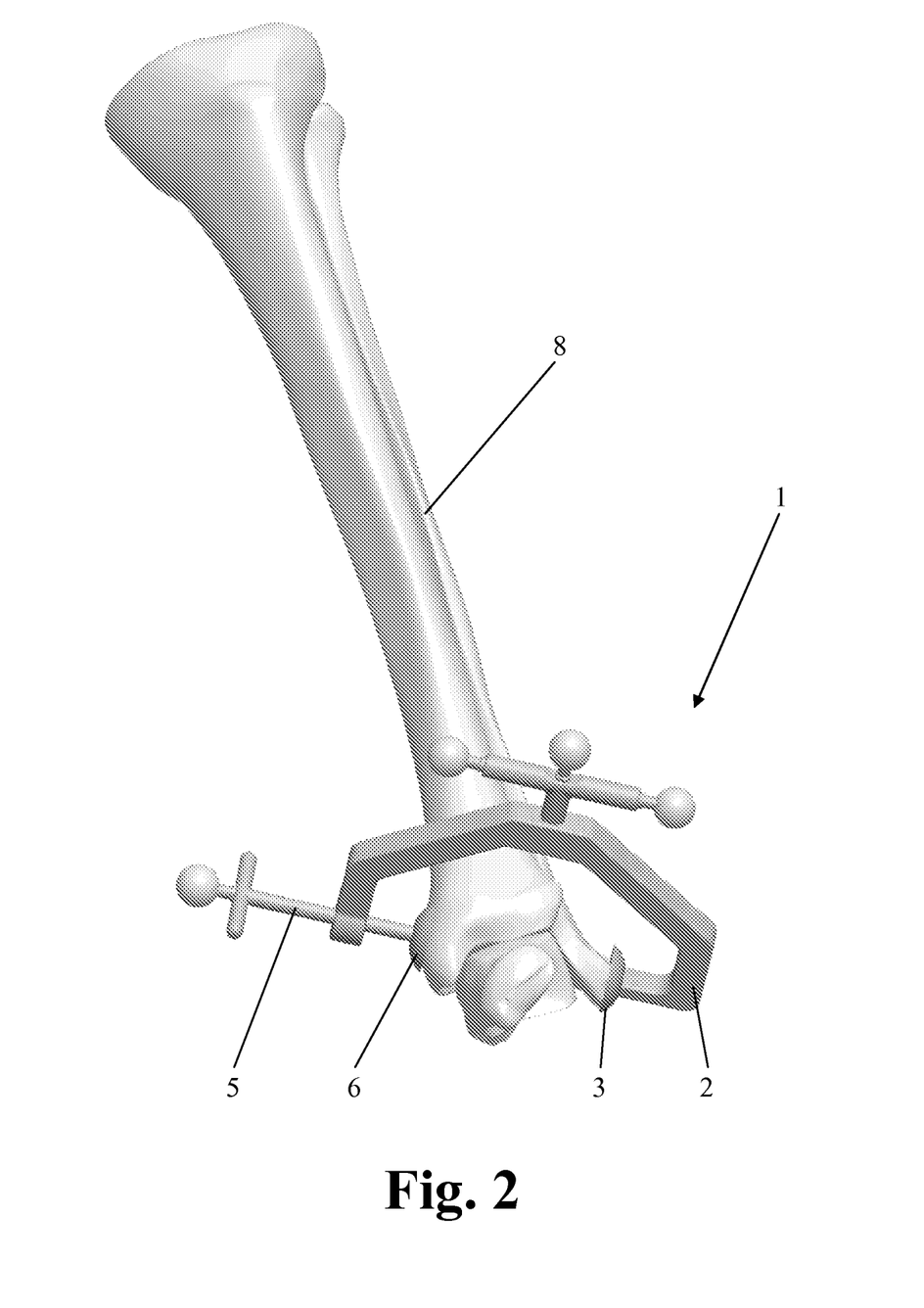
FIG. 2 the clamp of FIG. 1, attached to an ankle.

FIG. 2 shows the malleolar registration clamp 1 of FIG. 1, attached to the ankle of a lower leg 8. The lateral malleolus of the lower leg 8 is received in the receiving portion 3 of the first clamp body part 2, while the medial malleolus is received in the second receiving portion 6 of the second clamp body part 5.

One preferred way of applying the malleolar registration clamp is to place the receiving portion 3 of the first clamp body part 2 on one malleolus, for example on the lateral malleolus as shown in FIG. 2, such that the malleolus is in a defined position relative to the first clamp body part 2. This is achieved by the self-centering design of the receiving portion 3. When the receiving portion 3 of the first clamp body part 2 is pressed against the malleolus, the malleolus glides on the slope of the receiving portion 3 until it reaches an end position. This end position is defined and known relative to the first clamp body part 2.

The malleolar registration clamp is then tightened, which means that the second clamp body part 5 is rotated within the thread of the first clamp body part 2 until the second malleolus—in FIG. 2, the medial malleolus—has reached its end position within the second receiving portion 6 of the second clamp body part 5. This is again achieved by the malleolus gliding over the flank of the second receiving portion 6. Reducing the distance between the receiving portion 3 and the second receiving portion 6 creates forces which force the malleoli into their end positions within the receiving portion 3 and the second receiving portion 6, respectively.

In the embodiment shown in FIG. 1, the receiving portion 3 and the second receiving portion 6 each comprise an opening or recess which is rotationally symmetrical. Preferably, the receiving portion 3 and the second receiving portion 6 are positioned such that their two axes of symmetry are identical. This axis of symmetry is also preferably the same as the longitudinal axis of the screw-like second clamp body part 5.

Figure 3:
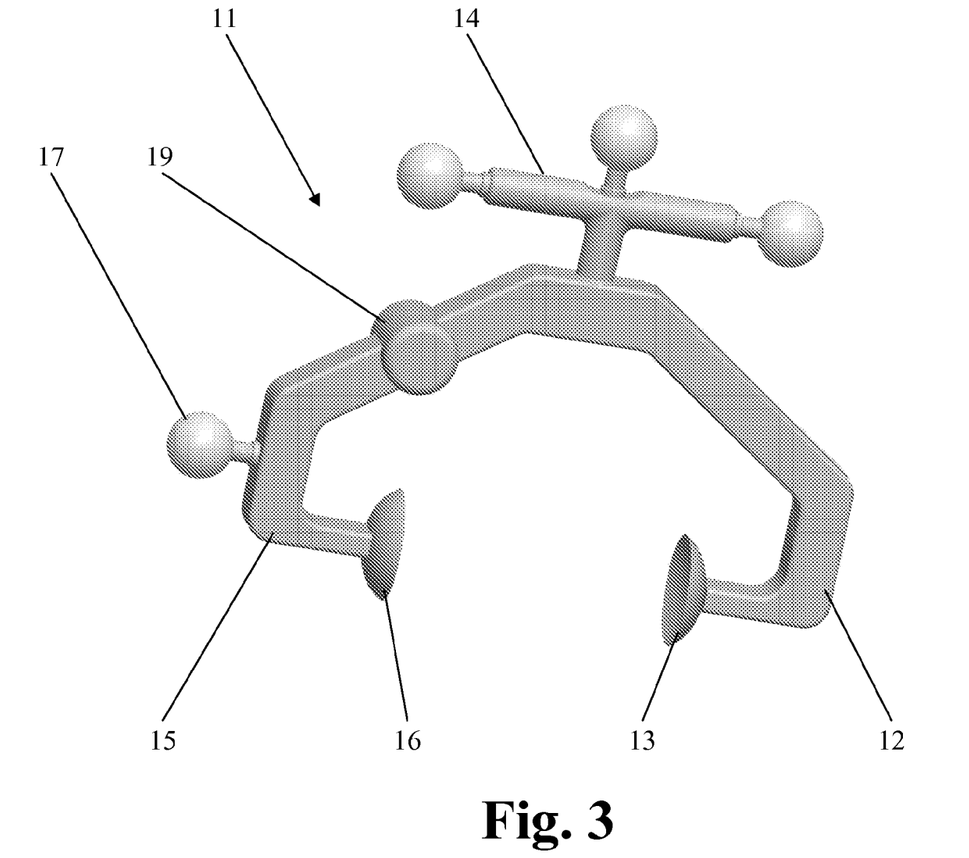
FIG. 3 a second embodiment of a malleolar registration clamp.

FIG. 3 shows a malleolar registration clamp 11 in accordance with a second embodiment. Like the malleolar registration clamp 1, the malleolar clamp 11 comprises a first clamp body part 12 and a second clamp body part 15, wherein a (first) reference unit 14 and a (first) receiving portion 13 are attached to the first clamp body part 12 and a second registration unit 17 and a second receiving portion 16 are attached to the second clamp body part 15. Contrary to the first embodiment, the two clamp body parts 12 and 15 together form a clamp body which is C-shaped. The openings or recesses of the receiving portion 13 and the second receiving portion 16 face each other. The two clamp body parts 12 and 15 are connected via a hinge joint 19 which allows a rotational relative movement between the two clamp body parts 12 and 15 about one axis only.

When the second clamp body part 15 is moved relative to the first clamp body part 12, the second reference unit 17—which in the present embodiment is a single marker sphere—follows a trajectory which is a circular arc about the hinge joint 19, i.e. the position of the second reference unit 17 relative to the (first) reference unit 14 is restricted, such that one marker sphere is sufficient as the second reference unit 17.

Like the receiving portions 3 and 6 of the clamp 1, the receiving portion 13 and the second receiving portion 16 of the clamp 11 have openings or recesses which are rotationally symmetrical and in particular form a spherical segment as shown in FIG. 3. The malleolar registration clamp 11 is preferably dimensioned such that the distance between the deepest points in the recesses of the receiving portion 13 and the second receiving portion 16 is essentially equal to the distance between the malleoli to be registered when the two axes of symmetry of the two receiving portions 13 and 16 are parallel, and preferably identical, to each other. This results in an optimum fit of the malleolar registration clamp 11.

Figure 4:
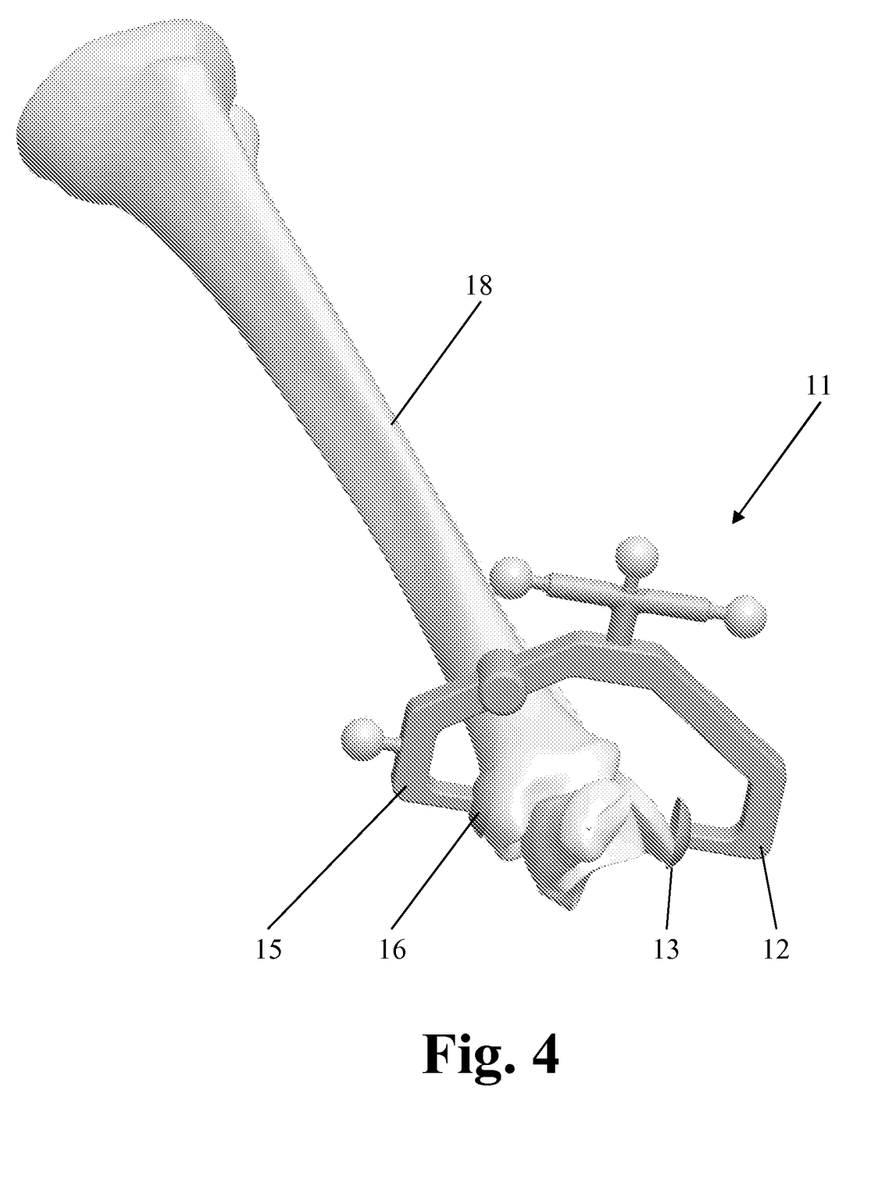
FIG. 4 the clamp of FIG. 3, attached to an ankle.

FIG. 4 shows the malleolar registration clamp 11, attached to an ankle of the lower leg 18. In this state, the receiving portion 13 and the second receiving portion 16 press against the lateral malleolus and medial malleolus, respectively, such that the lateral malleolus has a defined position relative to the first receiving portion 13 and the medial malleolus has a defined position relative to the second receiving portion 16.

A preferred way of applying the malleolar registration clamp 11 is to first splay the first clamp body part 2 and the second clamp body part 15 via the hinge joint 19, such that the distance between the receiving portion 13 and the second receiving portion 16 increases. The receiving portion 13 is then placed onto one of the malleoli, as already described for the receiving portion 3 of the clamp 1. The clamp 11 is then closed by rotating the second clamp body part 15 relative to the first clamp body part 12 about the hinge joint 19, such that the other malleolus is in a defined position relative to the second receiving portion 16.

If the hinge joint 19 is spring-loaded, the clamp 11 is splayed against the force of the spring, and the clamp 11 is automatically closed by the force of the spring. A manual adjustment of the clamp 11 is then unnecessary.

As the second receiving portion 16 approaches the second malleolus, the second malleolus is automatically centered as explained with regard to the second receiving portion 6 of the clamp 1 in accordance with the first embodiment. The only difference here is that the second receiving portion 16 approaches on a trajectory which describes a circular arc, rather than a linear trajectory as with the second receiving portion 6 of the clamp 1.

For ease of comprehension, only the bones of the legs 8 and 18 are shown in FIGS. 2 and 4. A conspicuous advantage of the malleolar registration clamp 1 or 11 in accordance with the present invention is that the clamp can be fixed on the ankle in a non-invasive manner, i.e. without any incision, since the malleoli are apparent through the skin and can be received within the receiving portions in a defined position relative to the receiving portion(s).

For registering a malleolus, the malleolar registration clamp is applied such that the malleolus is in a defined position relative to the clamp body. If the clamp 1 or 11 is a two-part clamp, the clamp is applied such that one malleolus is in a defined position relative to the first receiving portion and the other malleolus is in a defined position relative to the second receiving portion. If only one malleolus is to be registered, it is sufficient for this malleolus only to be in a defined position relative to the clamp body or a part of the clamp body. Once the clamp has been applied correctly, appropriate contact data are provided, for example by pressing a key or button. Alternatively, the contact data can be generated automatically, for example when the clamp remains untouched for a determined amount of time.

In a second step, the position of the first reference unit 4 or 14 is detected. As a result, reference unit position data are provided. Detecting the position of a reference unit is well-known in the prior art and a detailed description is therefore omitted here. Receiving portion position data representing the position of the receiving portion 3 or 13 relative to the reference unit 4 or 14, and malleolar position data representing the position of the malleolus relative to the receiving portion, are also provided. These data are for example retrieved from a memory or database.

In a final step, the malleolus is registered by calculating the malleolar position from the reference unit position data, the receiving portion position data and the malleolar position data, if the contact data indicate that the malleolus has been received in a defined position relative to the receiving portion, i.e. the position is calculated from the position of the reference unit 4 or 14, the relative position between the reference unit 4 or 14 and the first receiving portion 3 or 13 and the relative position between the first receiving portion 3 or 13 and the malleolus. Since these two relative positions are known, the position of the malleolus can be deduced from the position of the reference unit and the two dependent relative positions. Since the receiving portion 3 or 13 of the first clamp body part 2 or 12 is rotationally symmetrical, only the location of the malleolus can be calculated and not the orientation. However, knowing the spatial location of a malleolus is sufficient in most cases.

If both malleoli are to be registered, the position of the second reference unit 7 or 17 is calculated, for example based on the position of the first reference unit 4 or 14. This position is provided as second reference unit position data. The position of the reference unit 4 or 14 is determined first. Then, the position of the second reference unit 7 or 17 can be determined, based on the position of the first reference unit 4 or 14, since the freedom of movement of the second reference unit 7 or 17 relative to the reference unit 4 or 14 is constrained.

Second receiving portion position data representing the position of the second receiving portion 6 or 16 relative to the second reference unit 7 or 17, and second malleolar position data representing the position of the second malleolus relative to the second receiving portion 6 or 16, are also provided. These data are for example retrieved from a memory or database. Second contact data, indicating whether or not the second malleolus has been received within the second receiving portion 6 or 16 in a defined position relative to the second receiving portion, can be provided together with the (first) contact data. The (first) contact data and the second contact data can for example be identical or the same data.

The second malleolus is then registered by calculating the malleolar position from the second reference unit position data, the second receiving portion position data and the second malleolar position data, if the second contact data indicate that the second malleolus has been received in a defined position relative to the second receiving portion, i.e. the second malleolus is registered by calculating the malleolar position from the position of the second reference unit 7 or 17, the relative position between the second reference unit 7 or 17 and the second receiving portion 6 or 16 and the relative position between the second receiving portion 6 or 16 and the malleolus. With respect to the other malleolus, only its spatial location can be calculated if the second receiving portion 6 or 16 is rotationally symmetrical. However, if the spatial location of both malleoli is known, the malleolar axis can also be calculated from these spatial locations. The malleolar axis represents information which is often needed for surgical applications.

Figure 5:
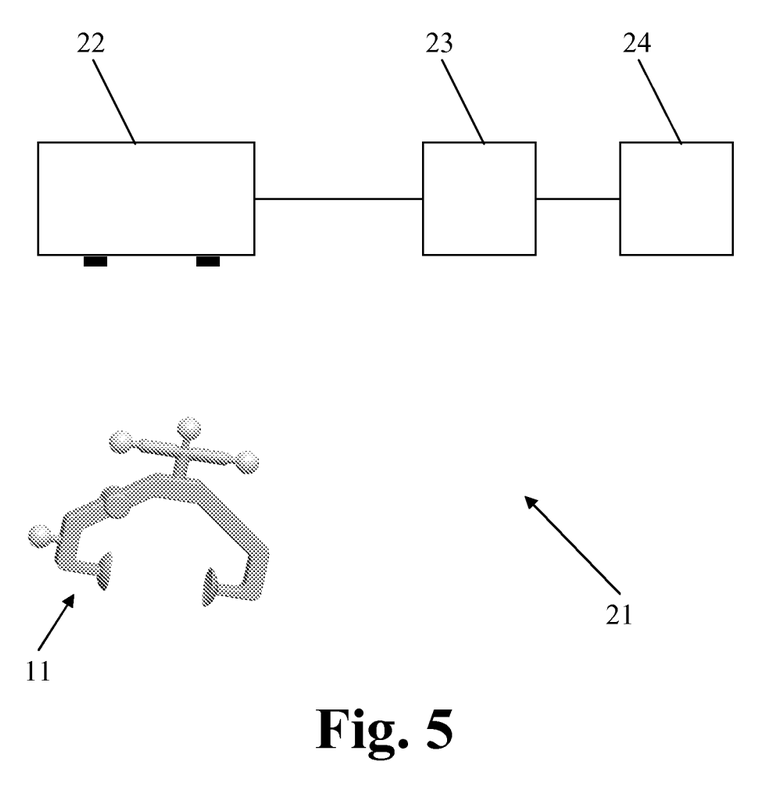
FIG. 5 a malleolar registration system.

FIG. 5 shows a malleolar registration system 21 comprising: a malleolar registration clamp 11; a registration unit 22 for registering the position of the reference units 14 and 17 of the clamp 11; and a processor 23 for registering the malleolus, as explained above. The registration unit 22 is a 3D infrared camera which generates a stereoscopic view of the reference units 14 and 17. The positions of the reference units 14 and 17 can be calculated from this stereoscopic view, either directly in the camera 22 or in the processor 23. The processor 23 is therefore designed to carry out the detecting and registering steps of the inventive method, for example by means of a computer program executed by the processor 23.

An output unit 24 is preferably connected to the processor 23. The output unit 24 can be a display device, such as a CRT or LCD monitor, for displaying the position of the malleolus or the positions of both malleoli and/or the malleolar axis. Alternatively, the output unit 24 can be an interface for connecting the processor 23 to another device which uses the result of the registration process, such as for example a navigation system. Instead of the malleolar registration clamp 11, the malleolar registration clamp 1 or any other clamp in accordance with the present invention can be used within the malleolar registration system 21. The receiving portions can have any suitable shape.

The invention claimed is:

1. A malleolar registration method using a malleolar registration clamp comprising a clamp body comprising first and second clamp body parts exhibiting a variable relative position, the first clamp body part comprising a first reference unit and a first receiving portion for receiving an associated first malleolus, wherein the first receiving portion is configured to receive at least part of the first malleolus in a defined position relative to the first receiving portion, and wherein a relative position between the first reference unit and the first receiving portion is fixed; and the second clamp body part comprising a second receiving portion for receiving an associated second malleolus in a defined position relative to the second receiving portion and comprising a second reference unit, wherein a relative position between the second reference unit and the second receiving portion is fixed, and wherein the second reference unit is a single marker sphere, the method, comprising:

provide first reference unit position data representing the position of the first reference unit;

providing first contact data indicating whether or not the first malleolus has been received within the first receiving portion of the malleolar registration clamp in a defined position relative to the first receiving portion;

providing first receiving portion position data representing the position of the first receiving portion relative to the first reference unit;

providing first malleolar position data representing the position of the first malleolus relative to the first receiving portion;

registering the first malleolus by calculating the position of the first malleolus from the first reference unit position data, the first receiving portion position data and the first malleolar position data, if the first contact data indicate that the first malleolus has been received in a defined position relative to the first receiving portion;

providing second contact data indicating whether or not a second malleolus has been received within the second receiving portion of the registration clamp in a defined position relative to the second receiving portion;

providing second malleolar position data representing the position of the second malleolus relative to the second receiving portion;

providing second reference unit position data representing the position of the second reference unit along a known trajectory; and registering the second malleolus by calculating the malleolar position from the second reference unit position data, the second receiving portion position data and the second malleolar position data, if the second contact data indicate that the second malleolus has been received in a defined position relative to the second receiving portion.

2. The malleolar registration method according to claim 1, wherein the second reference unit position data are derived from the reference unit position data and the position of the second reference unit relative to the reference unit.

3. A non-transitory computer readable storage medium comprising a computer program which, when running on a computer or loaded onto a computer, causes the computer to:

provide first reference unit position data representing the position of a first reference unit of a malleolar registration clamp comprising first and second clamp body parts exhibiting a variable relative position, the first clamp body part comprising a first reference unit and a first receiving portion for receiving an associated first malleolus, wherein the first receiving portion is configured to receive at least part of the first malleolus in a defined position relative to the first receiving portion, and wherein a relative position between the first reference unit and the first receiving portion is fixed; and the second clamp body part comprising a second receiving portion for receiving an associated second malleolus in a defined position relative to the second receiving portion and comprising a second reference unit, wherein a relative position between the second reference unit and the second receiving portion is fixed, and wherein the second reference unit is a single marker sphere;

provide first contact data indicating whether or not the first malleolus has been received within the first receiving portion of the malleolar registration clamp in a defined position relative to the first receiving portion;

provide first receiving portion position data representing the position of the first receiving portion relative to the first reference unit;

provide first malleolar position data representing the position of the first malleolus relative to the first receiving portion;

register the first malleolus by calculating the position of the first malleolus from the first reference unit position data, the first receiving portion position data and the first malleolar position data, if the first contact data indicate that the first malleolus has been received in a defined position relative to the first receiving portion;

provide second contact data indicating whether or not a second malleolus has been received within the second receiving portion of the registration clamp in a defined position relative to the second receiving portion;

provide second malleolar position data representing the position of the second malleolus relative to the second receiving portion;

provide second reference unit position data representing the position of the second reference unit along a known trajectory; and register the second malleolus by calculating the malleolar position from the second reference unit position data, the second receiving portion position data and the second malleolar position data, if the second contact data indicate that the second malleolus has been received in a defined position relative to the second receiving portion.

4. A computer comprising the non-transitory computer readable storage medium of claim 3.

5. A malleolar registration system comprising a clamp comprising a clamp body comprising first and second clamp body parts exhibiting a variable relative position, the first clamp body part comprising a reference unit and comprising a receiving portion for receiving a malleolus, wherein the receiving portion is designed to receive at least part of the malleolus in a defined position relative to the receiving portion, and the position of the reference unit relative to the receiving portion is fixed, and the second clamp body part comprising a second receiving portion for receiving a second malleolus in a defined position relative to the second receiving portion and comprising a second reference unit, wherein the position of the second reference unit relative to the second receiving portion is fixed and the second reference unit is a single marker sphere, a registration unit for registering the position of the reference units and the computer according to claim 4.

* * * * *